United States Patent
Koch et al.

(10) Patent No.: US 9,719,974 B2
(45) Date of Patent: Aug. 1, 2017

(54) MOISTURE SENSING DEVICE FOR GRAIN HANDLING

(71) Applicant: Sukup Manufacturing Co., Sheffield, IA (US)

(72) Inventors: Matthew R. Koch, Clear Lake, IA (US); Kerry Hartwig, Iowa Falls, IA (US); Graham Giddings, Sheffield, IA (US); Mitchell Meier, Mason City, IA (US)

(73) Assignee: Sukup Manufacturing Co., Sheffield, IA (US)

( * ) Notice: Subject to any disclaimer, the term of this patent is extended or adjusted under 35 U.S.C. 154(b) by 215 days.

(21) Appl. No.: 14/031,121

(22) Filed: Sep. 19, 2013

(65) Prior Publication Data
US 2015/0075263 A1   Mar. 19, 2015

(51) Int. Cl.
*G01N 19/10*   (2006.01)
*G01N 33/10*   (2006.01)

(52) U.S. Cl.
CPC .................... *G01N 33/10* (2013.01)

(58) Field of Classification Search
CPC ...................................... F26B 25/22
See application file for complete search history.

(56) References Cited

U.S. PATENT DOCUMENTS

| | | | |
|---|---|---|---|
| 3,714,718 A | 2/1973 | Sukup | |
| 4,750,273 A * | 6/1988 | Parkes | F26B 25/22 34/484 |
| 4,896,795 A * | 1/1990 | Ediger | F26B 25/22 222/52 |
| 4,916,830 A | 4/1990 | Braun et al. | |
| 5,092,819 A * | 3/1992 | Schroeder | A01D 41/127 460/7 |
| 5,189,812 A | 3/1993 | Ediger | |
| 5,934,997 A * | 8/1999 | Nelson | G01F 1/663 460/149 |
| 5,957,773 A * | 9/1999 | Olmsted et al. | 460/7 |
| 6,440,475 B1 * | 8/2002 | McNeff | G01N 25/56 426/231 |
| 8,123,452 B2 * | 2/2012 | Sukup | A01F 25/186 239/687 |
| 9,015,958 B2 * | 4/2015 | Bloemendaal | F26B 3/06 324/664 |
| 2010/0229421 A1 | 9/2010 | Salisbury | |
| 2013/0014404 A1 | 1/2013 | Bloemendaal | |

* cited by examiner

*Primary Examiner* — Lisa Caputo
*Assistant Examiner* — Tran M Tran
(74) *Attorney, Agent, or Firm* — Zarley Law Firm, P.L.C.

(57) ABSTRACT

A moisture sensing device having an elongated chute with an open top and a gate at the bottom. The gate is connected to an actuator for opening and closing the gate. A proximity sensor is mounted to the chute adjacent the gate to detect whether the gate is open or closed. Connected to and extending into the chute is a moisture sensor. The moisture sensor, proximity sensor, and actuator are all connected to a controller.

19 Claims, 3 Drawing Sheets

MOISTURE SENSING DEVICE FOR GRAIN HANDLING

BACKGROUND OF THE INVENTION

This invention is directed to a device for sensing moisture in grain and more particularly to a device for measuring moisture in a static sample of grain.

Devices for sensing moisture in grain are known in the art. Typically, existing sensing devices are mounted at the end of a discharge conveyor and take a measurement of a dynamic sample as grain continuously flows past the sensor. The problem with measuring a dynamic sample is that the grain flow must be restricted in order for a sufficient amount of grain to pass over the sensor to take a reading which causes the grain chute to plug. In addition, measuring a sample of moving grain is not as accurate as measuring a set volume of non-moving grain.

Alternatively, many elevators use table top moisture sensors that require a user to remove a sample of grain from the flow or discharge of grain to conduct a test, which is time consuming, inconvenient, and labor intensive. Therefore, a need exists in the art for a device that addresses these deficiencies.

An objective of the present invention is to provide a moisture sensing device for taking static measurements in a grain handling operation.

Another objective of the present invention is to provide a moisture sensing device for grain handling operations that is more accurate.

These and other objectives will be apparent to one of ordinary skill in the art based upon the following written description, drawings, and claims.

SUMMARY OF THE INVENTION

A moisture sensing device having an elongated chute with an open top and a gate at the bottom. The gate is connected to an actuator for opening and closing the gate. A proximity sensor is mounted to the chute adjacent the gate to detect whether the gate is open or closed. Connected to and extending into the chute is a moisture sensor. The moisture sensor, proximity sensor, and actuator are all connected to a controller.

DETAILED DESCRIPTION OF THE PREFERRED EMBODIMENTS

Figure 1:
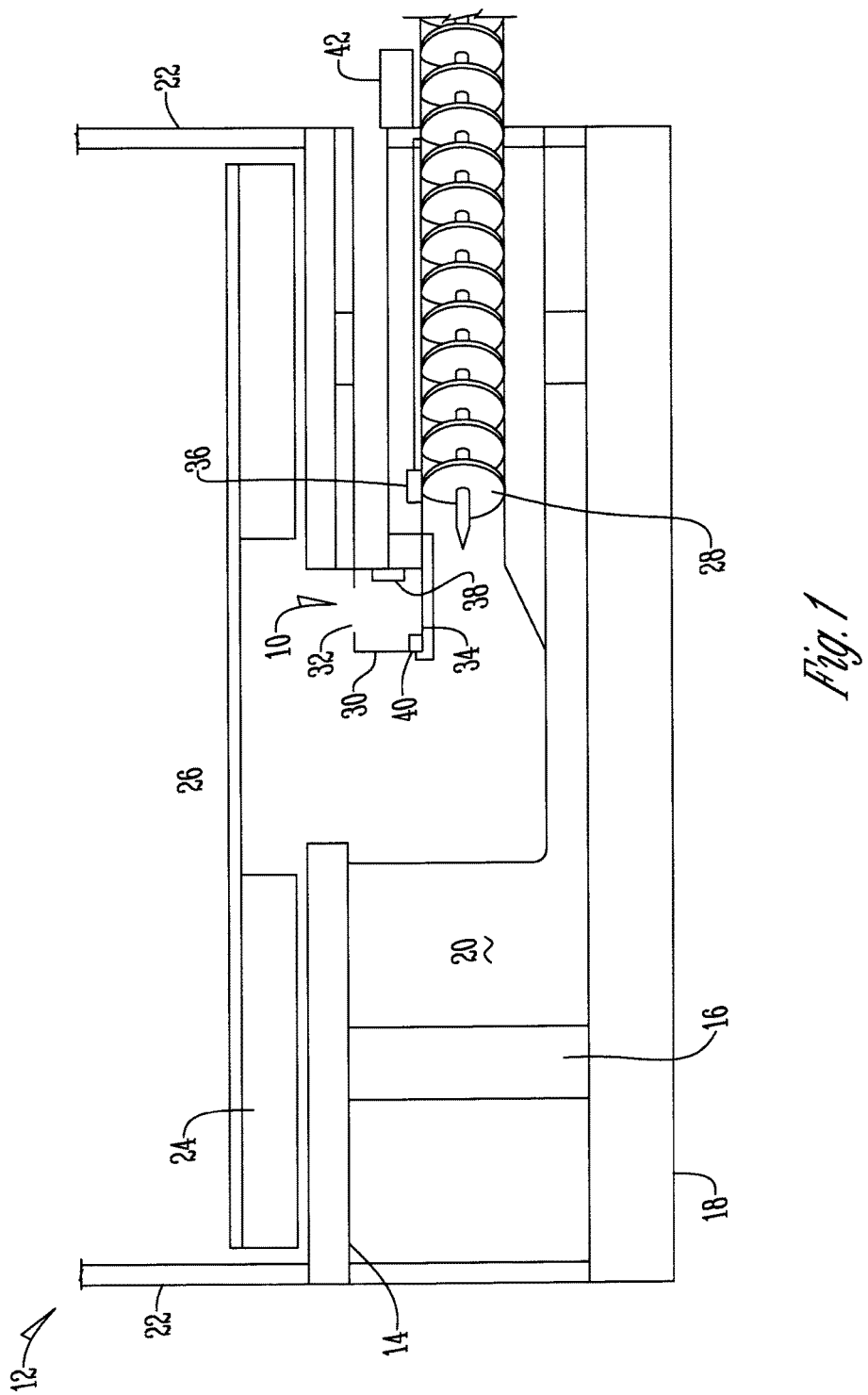
FIG. 1 is a side sectional view of a moisture sensing device in a grain dryer.
Figure 2:
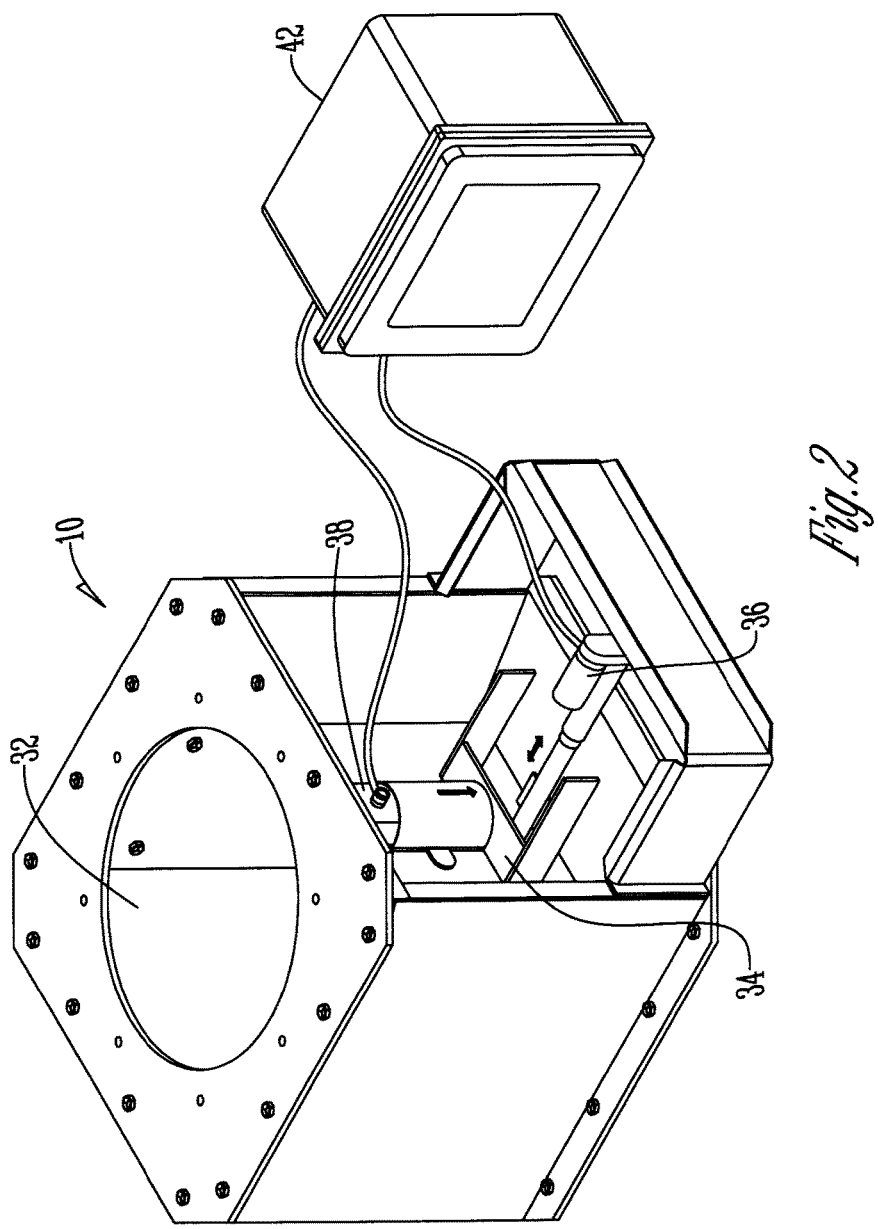
FIG. 2 is a perspective view of a moisture sensing device showing an actuator connected to a gate which closes a chute just below a sensor.
Figure 3:
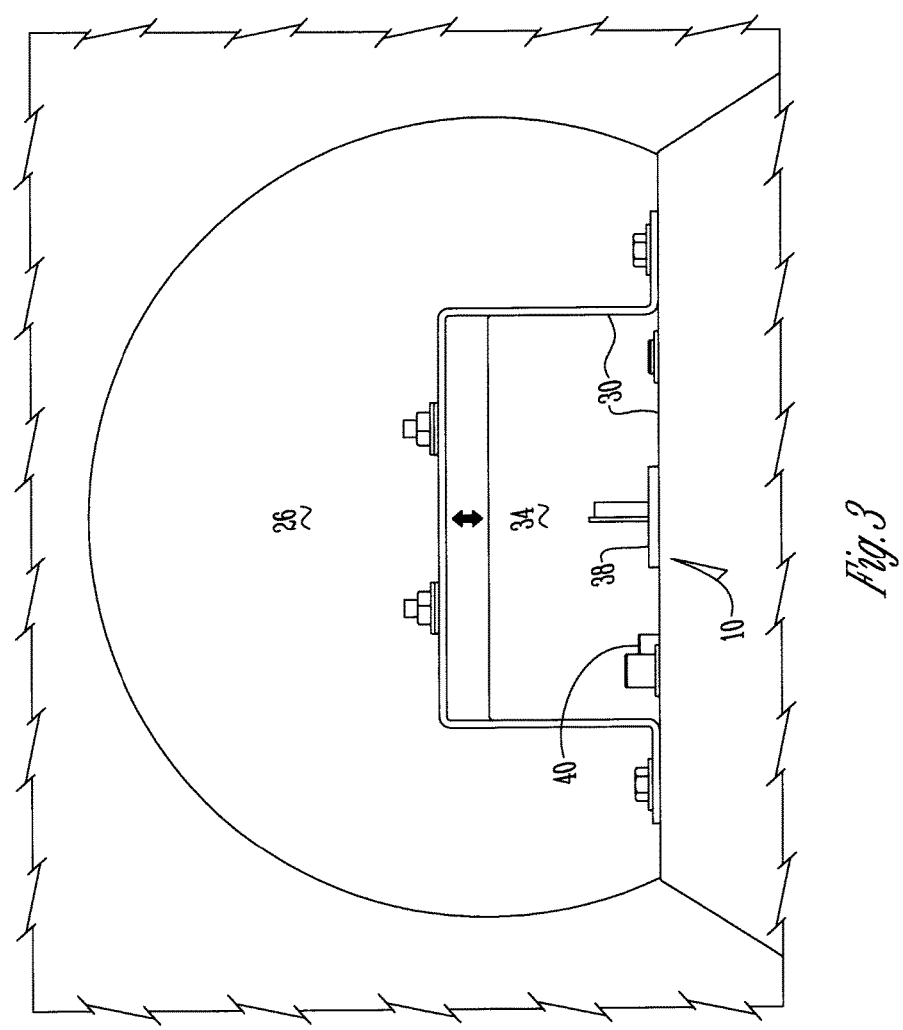
FIG. 3 is a top perspective view of a moisture sensing device with the gate in a partially opened and partially closed state.

Referring to the Figures a moisture sensing device 10 is mounted within a grain storage device 12, a grain moving device such as the path or a chute or auger, or a grain conditioning device such as a grain dryer or tower dryer. The moisture sensing device 10 is used with any grain handling operation including portable and stacked dryers and the like. The sensing device 10 is shown here in use with a tower dryer as an example only. The tower dryer 12 has a floor 14 mounted on supports 16 above a foundation 18. A chamber 20 is formed between the floor 14 and foundation and enclosed by a lower portion of a sidewall 22.

A sweep rotor 24 extends radially outward from the center of dryer 12 just above floor 14 and rotates about a center axis to sweep across floor 14 and feed grain from floor 14 into sump 26. Sump 26 is formed at the center of floor 14 for receiving grain which is then transported out of the dryer 12 using a screw conveyor 28 or the like.

The moisture sensing device 10 is mounted within the chamber 20 between the sump 26 and conveyor 28. The sensing device 10 includes a chute 30 having an open top 32 and a gate 34 at the bottom. The gate 34 is connected to an inward most end of actuator 36 such as a linear actuator or the like. A sensor 38 for detecting moisture in grain is attached to and extends into the chute 30. In one arrangement, sensor 38 is also enabled to detect any other attribute of the grain such as weight, density, temperature, or the like. Also, a proximity sensor 40 is attached near gate 34 to detect whether gate 34 is open or closed. The actuator 36, sensor 38, and proximity sensor 40 are all electrically connected to a controller 42 having a processor and memory and a display such as a touch screen monitor which displays results as well as the status of sensing device 10 (that is whether the sensing device 10 is on or off, whether the chute 30 is open or closed, whether the gate 34 has engaged the proximity sensor 40, etc.). In another embodiment, components of controller 42 are separated; that is, the processor and memory and other controlling components are positioned within a conventional electrical panel of the grain storage device or tower dryer 12, whereas the display, monitor or touch screen is located at a separate location, sometimes a distant location, by connection to the internet or an Ethernet cable, wireless connection or the like.

In operation, as grain is swept into sump 26 a portion or sample of the grain falls through the open top 32 of chute 30 while the gate 34 is closed and fills the chute 30 with grain. The moisture sensor 38 takes a measurement of the moisture in the grain, or any other attribute, and transmits the measurement to the controller 42. A measurement reading can be set to occur after a predetermined time, such as 20 seconds, has elapsed after gate 30 has been confirmed closed by the proximity sensor 40. Once a measurement has been received the controller 42 sends a signal to the actuator 38 causing the actuator 38 to open which allows grain to fall through the bottom of the chute 30 to conveyor 28. After a predetermined time delay, such as 20 seconds, the process is repeated.

In one arrangement the measurement cycle occurs in the following manner: The tower dryer 12 is started and grain continuously flows through sump 26. The gate 34 is actuated to close the bottom of the chute 30. Once closed, grain begins to fill the sensing device 10. The sensing device 10 is programmed to allow 20 seconds to pass before beginning measurements (however any other amount of time is hereby contemplated). This is time is allowed such that at the lowest grain flow rate the sensing device 10 will be full of grain. After the sensing device 10 fills with grain, additional grain piles-up or towers on top of the sensing device 10 with the extra grain simply sliding off of the sensing device 10 into the conveyor 28. Once the allotted amount of time passes the controller 42 begins the measurement procedure, which includes sampling the grain twice a second for 20 seconds for a total of 40 measurements (however any other amount of time and frequency is hereby contemplated) with the results being sent to the controller 42 either individually or aggregated. Once the measurement procedure is completed, the controller 42 opens the gate 34, the grain is dumped and the process is repeated. In one arrangement, the cycle time is one completed cycle per minute (however any other cycle time is hereby contemplated).

As the controller receives multiple moisture measurements, the controller 42 calculates an average which is displayed to an operator, among any other information.

Thus, a moisture sensing device has been disclosed that, at the very least, meets all the stated objectives.

It will be appreciated by those skilled in the art that other various modifications could be made to the device without parting from the spirit and scope of this invention. All such modifications and changes fall within the scope of the claims and are intended to be covered thereby.

What is claimed:

1. A device for measuring moisture in grain, comprising: a chamber positioned between a sump and a conveyor; a chute mounted within the chamber and having an open top and a gate at a bottom of the chute, wherein the open top is configured to receive a portion of grain flowing into the chamber through the sump; an actuator connected to the gate; a moisture sensor attached to and extending into the chute; a controller connected to the actuator and the moisture sensor; and a proximity sensor mounted adjacent to the gate and connected to the controller.

2. The device of claim 1 wherein the moisture sensor takes a moisture measurement after a predetermined time has elapsed after the proximity sensor detects that the gate is closed.

3. The device of claim 2 wherein the actuator opens the gate after a predetermined amount of time has elapsed after the moisture sensor has taken a measurement.

4. The device of claim 3 wherein the actuator closes the gate after a predetermined amount of time has elapsed after the actuator has opened the gate.

5. The device of claim 1 wherein the actuator is linear.

6. The device of claim 1 wherein the moisture sensor is configured to determine the weight, density, and temperature.

7. The device of claim 1 further comprising the controller having a processor, memory, and a display.

8. The device of claim 7 wherein the display is a touch screen.

9. The device of claim 7 wherein the display is separate and remote of the controller.

10. The device of claim 7 wherein the display of the controller displays a status of the moisture sensor.

11. The device of claim 1 wherein the controller is configured to calculate an average moisture.

12. The device of claim 1 wherein the moisture sensor is configured to sample twice a second when sampling.

13. The device of claim 12 wherein the moisture sensor is configured to send sampling results individually to the controller.

14. The device of claim 12 wherein the moisture sensor is configured to send sampling results in the aggregate to the controller.

15. The device of claim 1 wherein the moisture sensor is configured to sample for 20 seconds per sampling cycle.

16. The device of claim 1 wherein the chamber is formed between a floor and a foundation of a grain bin and enclosed by a lower portion of a sidewall.

17. The device of claim 1 wherein when the gate is in a closed position the chute fills with the portion of the grain, while an excess portion of the grain accumulates above the moisture sensor and slides off through the chamber.

18. A device for measuring moisture in grain, comprising: a chamber formed between a floor and a foundation of a grain bin and enclosed by a lower sidewall; a chute mounted between a sump and a conveyor within the chamber, wherein the chute has an open top and a gate at a bottom of the chute; an actuator connected to the gate; a moisture sensor configured to determine the moisture, weight, density, and temperature of grain attached to and extending into the chute; a controller connected to the actuator and the moisture sensor; and a proximity sensor mounted adjacent to the gate and connected to the controller.

19. A device for measuring moisture in grain, comprising: a chamber positioned between a sump and a conveyor; a chute mounted within the chamber and having an open top and a gate at a bottom of the chute, wherein the open top is configured to receive a portion of grain flowing into the chamber through the sump; an actuator connected to the gate; a moisture sensor attached to the chute; a controller connected to the actuator and the moisture sensor; and a proximity sensor mounted adjacent to the gate and connected to the controller, wherein when the gate is in a closed position the chute fills with a portion of grain while an excess portion of the grain accumulates above the moisture sensor and slides off the chamber through the chamber to the conveyor below.

* * * * *